United States Patent
Shibuya et al.

(10) Patent No.: US 7,214,796 B2
(45) Date of Patent: May 8, 2007

(54) PROCESS FOR PRODUCTION OF 1-[2-(BENZIMIDAZOL-2-YL-THIO)ETHYL] PIPERAZINE OR SALTS THEREOF

(75) Inventors: Kimiyuki Shibuya, Saitama (JP); Yukihiro Sato, Tokyo (JP)

(73) Assignee: Kowa Co., Ltd., Nagoya-shi (JP)

( * ) Notice: Subject to any disclaimer, the term of this patent is extended or adjusted under 35 U.S.C. 154(b) by 160 days.

(21) Appl. No.: 10/535,705

(22) PCT Filed: Nov. 27, 2003

(86) PCT No.: PCT/JP03/15154

§ 371 (c)(1),
(2), (4) Date: May 20, 2005

(87) PCT Pub. No.: WO2004/048342

PCT Pub. Date: Jun. 10, 2004

(65) Prior Publication Data
US 2006/0035906 A1 Feb. 16, 2006

(30) Foreign Application Priority Data
Nov. 28, 2002 (JP) ............................. 2002-346114

(51) Int. Cl.
C07D 235/28 (2006.01)
C07D 403/12 (2006.01)
(52) U.S. Cl. ..................... 544/370; 544/386
(58) Field of Classification Search ................ None
See application file for complete search history.

(56) References Cited

U.S. PATENT DOCUMENTS

| 3,585,194 | A | 6/1971 | Leister |
| 5,068,264 | A | 11/1991 | Mueller et al. |
| 6,969,711 | B2 * | 11/2005 | Shibuya et al. ............. 514/218 |
| 6,998,486 | B2 * | 2/2006 | Shibuya et al. ............. 544/368 |
| 2004/0038987 | A1 | 2/2004 | Shibuya et al. |
| 2004/0176593 | A1 | 9/2004 | Shibuya et al. |
| 2005/0032814 | A1 | 2/2005 | Shibuya et al. |

FOREIGN PATENT DOCUMENTS

| DE | 2 209 853 | 9/1972 |
| EP | 0 334 818 | 9/1989 |
| WO | 98/54153 | 12/1998 |
| WO | 03/057675 | 7/2003 |

OTHER PUBLICATIONS

U.S. Appl. No. 10/535,705, filed May 20, 2005, Shibuya et al.
Rashmi Rastogi, et al., "Synthesis of 2-Substituted Thiobenzimidazoles as Potential Anthelminthics", Arch. Pharm. (Weinheim), XP-002963488, vol. 316, No. 7, 1983, pp. 638-643.

* cited by examiner

Primary Examiner—Emily Bernhardt
(74) Attorney, Agent, or Firm—Oblon, Spivak, McClelland, Maier & Neustadt, P.C.

(57) ABSTRACT

This invention relates to a method for producing 1-[2-(benzimidazol-2-ylthio)ethyl]piperazine (5) or its salt by the following reaction scheme:

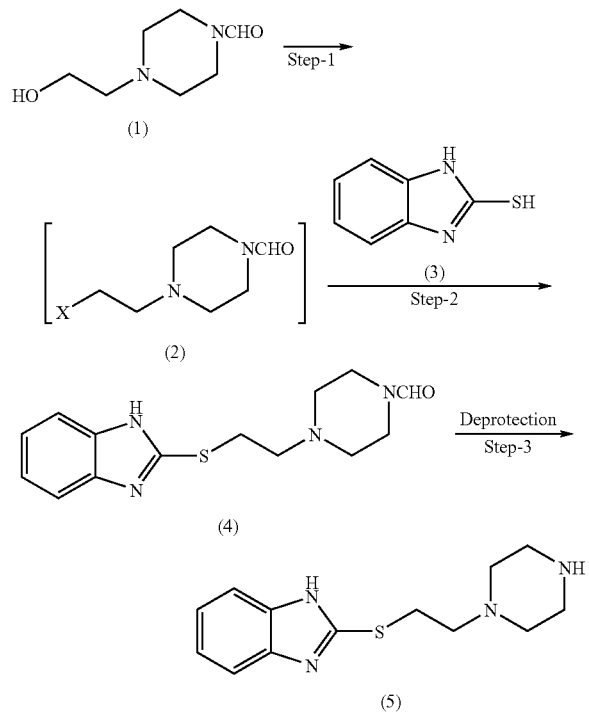

This invention enables efficient production of 1-[2-(benzimidazol-2-ylthio) ethyl]piperazine or its salt which is an intermediate in the production of a cyclic diamine compound which is useful as a ACAT inhibitor.

2 Claims, No Drawings

PROCESS FOR PRODUCTION OF 1-[2-(BENZIMIDAZOL-2-YL-THIO)ETHYL] PIPERAZINE OR SALTS THEREOF

TECHNICAL FIELD

This invention relates to a method for producing 1-[2-(benzimidazol-2-ylthio)ethyl]piperazine or its salt, which is an intermediate in producing ACAT inhibitor.

BACKGROUND OF THE INVENTION

Acyl coenzyme A: cholesterol acyltransferase (ACAT) is an enzyme which catalyzes synthesis of cholesterol ester from cholesterol, and it plays an important role in the metabolism of the cholesterol and its absorption from the digestive tract.

Recent studies have revealed that elevation of blood cholesterol level can be effectively suppressed by inhibiting the activity of ACAT in small intestine and liver, and quite a number of studies have been conducted on ACAT inhibitor.

On the other hand, the present inventors focused the study on ACAT in vascular wall, and studied on the selective inhibitors against this type of ACAT. It was then found that azole compounds having a cyclic diamine structure, and in particular, a cyclic diamine compound represented by the following formula (7):

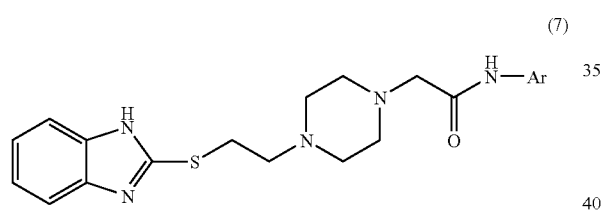

wherein Ar represents an optionally substituted aryl or heteroaryl group, as well as its salt exhibit reduced side effects, high solubility in water, and excellent oral absorption, and that such compound is well adapted for use as a therapeutic drug for hyperlipidemia and arteriosclerosis. As a result, the present inventors have filed a PCT application for an invention associated with azole compounds including the compound (7) (WO98/54153).

This patent application has demonstrated that the compound (7) can be produced by the method as represented by the following reaction scheme.

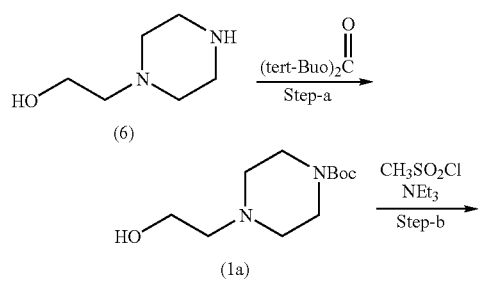

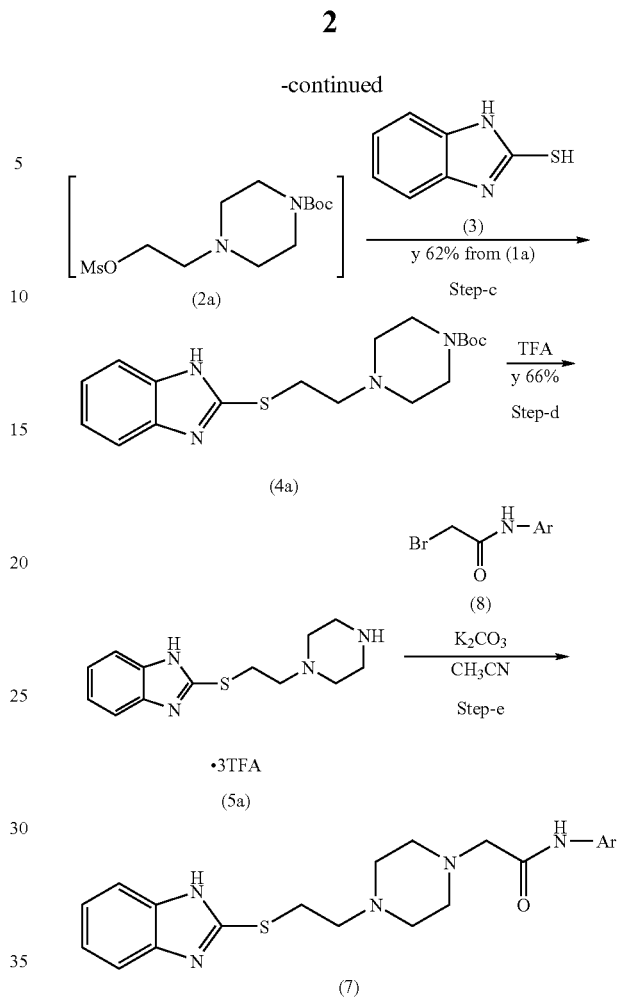

In this method, the compound (7) is produced in the five steps as described below by starting from 1-(2-hydroxyethyl) piperazine (6), namely, by protecting amino group of the 1-(2-hydroxyethyl) piperazine (6) with tert-butoxycarbonyl (Boc) group to produce 1-(tert-butoxycarbonyl)-4-(2-hydroxyethyl) piperazine (1a) (Step a); converting hydroxyl group of this compound (1a) to methanesulfonyloxy group to produce compound (2a) (Step b); reacting this compound (2a) with 2-mercaptobenzimidazole (3) in the presence of a base to produce 1-[2-(benzimidazol-2-ylthio)ethyl]-4-(tert-butoxycarbonyl) piperazine (4a) (Step c); removing the Boc group for deprotection by using trifluoroacetic acid to produce 1-[2-(benzimidazol-2-ylthio)ethyl]piperazine.3 trifluoroacetic acid (5a) (Step d); and reacting the compound (5a) with a bromo derivative (8) to thereby produce the compound (7) or its salt (Step e).

This production method, however, suffered from the problems including (i) di-tert-butyl dicarbonate, which is the expensive reagent used in the amino group protection; (ii) difficulty in Step a of purifying the target compound (1a) by distillation, which is the convenient purification method; (iii) difficulty of producing the compound (1a) in highly anhydrous condition as required by the following Step b because of the difficulty in the purification by distillation; (iv) poor stability of the mesyl derivative (2a) which is used as the starting material in Step c, and difficulty in reproducing the yield of the small scale synthesis in the large scale synthesis; and (v) insufficient yield in the deprotection reaction of Step d.

SUMMARY OF THE INVENTION

The present invention relates to provide an industrially advantageous method for producing 1-[2-(benzimidazol-2-ylthio)ethyl]piperazine (5) or its salt which is an intermediate in producing the cyclic diamine compound (7) or its salt.

In view of the situation as described above, the present inventors have made an intensive study, and found that, as shown in the following synthesis scheme, if 1-[2-(benzimidazol-2-ylthio)ethyl]piperazine or its salt (5) is produced by converting hydroxyl group of 1-formyl-4-(2-hydroxyethyl)piperazine (1) to benzimidazol-2-ylthio group, and then deprotecting formyl group, yield as well as purity can be improved by more convenient purification process compared to the process using Boc for the amino protective group. The present invention is based on such a finding.

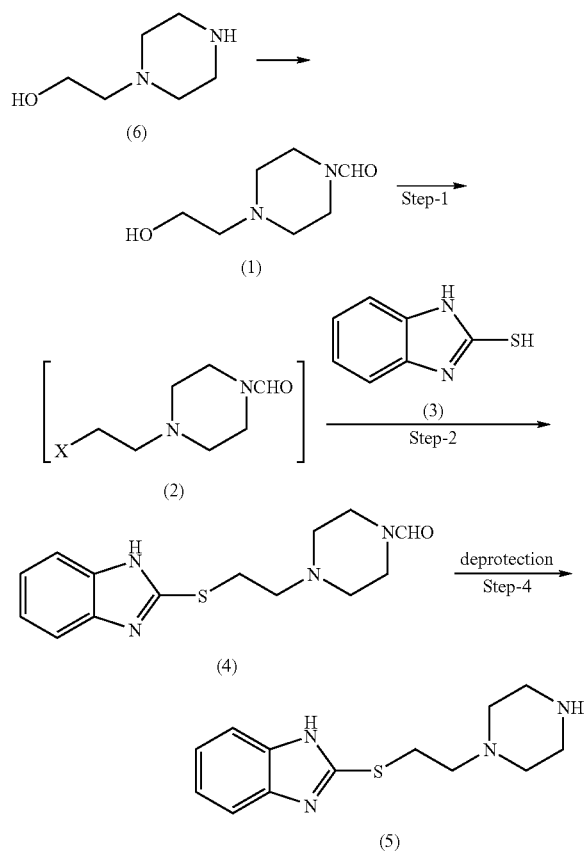

More specifically, the present invention provides a method for producing 1-[2-(benzimidazol-2-ylthio)ethyl]piperazine represented by formula (5) or its salt comprising the steps of converting hydroxyl group in 1-formyl-4-(2-hydroxyethyl)piperazine represented by formula (1) to a leaving group to produce a compound represented by formula (2), reacting this compound with 2-mercaptobenzimidazole (3) in the presence of a base to produce 1-[2-(benzimidazol-2-ylthio)ethyl]-4-formylpiperazine represented by formula (4), and detaching the formyl group to produce the 1-[2-(benzimidazol-2-ylthio)ethyl]piperazine represented by formula (5).

Use of the production method of the present invention will enable efficient production of the 1-[2-(benzimidazol-2-ylthio)ethyl]piperazine or its salt (5), and hence, the cyclic diamine compound (7) or its salt which is useful in medical applications is produced in a commercially more advantageous manner at a more stable yield compared to the conventional production method.

BEST EMBODIMENTS FOR CARRYING OUT THE INVENTION

The leaving group represented by "X" in the compound (2) of the present invention is a group like sulfonyloxy group or a halogen atom which is readily replaceable, and examples include sulfonyloxy groups such as methanesulfonyloxy, benzenesulfonyloxy, chloromethanesulfonyloxy, ethanesulfonyloxy, propanesulfonyloxy, and p-toluenesulfonyloxy, and halogen atoms such as chlorine atom, bromine atom, and iodine atom. Among them, preferred is methanesulfonyloxy group.

The compound (5) of the present invention may form an acid addition salt, and examples of such salt include inorganic acid salts such as hydrochloride, sulfate, nitrate, and phosphate, and organic acid salts such as methanesulfonate, maleate, fumarate, citrate, and trifluoroacetate.

In addition, the compound (5) is not limited to the non-salivate type, and also included are a hydrate and a solvate having water, alcohol, or other solvent used in the production and purification added thereto.

[Step 1]

Exemplary processes which may be used in converting the hydroxyl group of compound (1) to the leaving group include conversion of the hydroxyl group to a sulfonyloxy group or a halogen atom.

Typically, conversion to a sulfonyloxy group may be accomplished by reacting the compound (1) with chloride or anhydride of sulfonic acid in a solvent at a temperature of 0° C. to room temperature in the presence of a base.

Examples of the sulfonic acid in the sulfonic acid chloride or sulfonic acid anhydride include alkyl sulfonic acids such as methanesulfonic acid and ethanesulfonic acid and aryl sulfonic acids such as benzene sulfonic acid and p-toluenesulfonic acid.

Examples of the base used include triethylamine, N,N-diisopropylethylamine, pyridine, and 4-dimethyl aminopyridine, and examples of the solvent used include chloroform, methylene chloride, acetonitrile, tetrahydrofuran, ethyl acetate, benzene, toluene, and dimethylformamide.

The conversion of the hydroxyl group to a halogen atom is preferably accomplished by using a chlorinating or brominating agent such as phosphorus oxychloride, phosphorus pentachloride, triphenylphosphine dichloride, triphenylphosphine dibromide, triphenylphosphite dichloride, triphenylphosphite dibromide, phosphorus tribromide, thionyl chloride, or triphenylphosphine and carbon tetrachloride; triphenylphosphine and carbon tetrabromide; methanesulfonyl chloride and 4-dimethyl aminopyridine; and the like in the absence of the solvent or in the solvent such as dichloromethane, chloroform, dichloroethane, pyridine, or tetrahydrofuran at 0 to 120° C.

[Step 2]

The reaction between compound (2) and 2-mercaptobenzimidazole (3) may be accomplished in a solvent and in the presence or absence of a base and a catalyst.

The solvent used is not particularly limited, and examples include dimethyl formamide, dimethyl sulfoxide, methylene chloride, chloroform, tetrahydrofuran, toluene, acetone, and acetonitrile, which may be used alone or in combination of two or more.

Examples of the base used include inorganic bases, for example, alkaline metal hydroxides such as sodium hydroxide and potassium hydroxide; alkaline metal carbonates such as sodium carbonate and potassium carbonate; alkaline metal hydrogencarbonates such as sodium hydrogencarbonate and potassium hydrogencarbonate; as well as organic bases such as pyridine, triethylamine, N,N-diisopropylethylamine, N-methyl morpholine, and N,N-dimethylaniline.

Exemplary catalysts include crown ethers such as 18-crown-6 and quarternary ammonium salts such as tetrabutylammonium chloride, tetrabutylammonium bromide, tetrabutylammonium iodide, tetrabutylammonium hydrogensulfate, and benzyltrimethylammonium bromide. Among them, preferred is use of 18-crown-6.

The reaction is generally accomplished at 0 to 120° C., and preferably at 20 to 100° C. for 1 to 12 hours, and preferably for 1 to 3 hours.

The target compound (4) exhibits good crystallization, and it can be readily purified by crystallization. In addition, the target compound is obtainable by this reaction at a high yield and at a high purity in the industrial scale production, since the reaction in the small scale production is well reflected to such industrial scale production.

[Step 3]

The 1-[2-(benzimidazol-2-ylthio)ethyl]piperazine (compound (5)) or its salt can be obtained by removing the formyl group of the thus obtained compound (4).

The removing of the formyl group may be accomplished by adding an acid to the compound (4) in a solvent, and allowing the reaction to proceed at 0° C. to 100° C. The solvent used may be an alcoholic solvent such as methanol, ethanol, or isopropylalcohol, benzene, toluene, ethyl acetate, or the like, which may optionally contain water, and the acid used may be hydrochloric acid, sulfuric acid, or the like.

The cyclic diamine compound (7) or its salt can be produced at a high efficiency by introducing a bromo derivative (8) to the amino group of the thus obtained compound (5) or its salt in the presence of a base according to the method described in Patent Document 1.

The 1-formyl-4-(2-hydroxyethyl)piperazine (1), which is the starting material of the present invention, can be produced by converting amino group of 1-(2-hydroxyethyl) piperazine (6) to formyl group by a known method (Arzneim. Forsch 12, 937–941(1962)) using methyl formate. More specifically, methyl formate may be added to the compound (6), and the reaction may be allowed to proceed at room temperature to reflux temperature for 1 to 48 hours. Use of such reaction readily yields the compound (1) at a high yield and at a high purity when it is purified by distillation. In addition, use of methyl formate enjoys the merits of low cost and considerable commercial availability.

Alternatively, compound (1) may be synthesized by such reaction as the reaction of 1-formylpiperazine with ethylene oxide, or the reaction of 1-formylpiperazine with ethylene halohydrin or the ethylene halohydrin protected by hydroxyl group in the presence of a base, or the like (When the protected halohydrin is used, the reaction of the leaving group and the removal of the protective group are simultaneously conducted)

EXAMPLES

The present invention is described in further detail by referring to the following Examples.

Example 1

Production of 1-[2-(benzimidazol-2-ylthio)ethyl]-4-formylpiperazine 1-formyl-4-(2-hydroxyethyl)piperazine was synthesized from 1-(2-hydroxyethyl)piperazine by the method described in a document (Arzneim. Forsch 12, 937–941 (1962)). To a solution of 1-formyl-4-(2-hydroxyethyl)piperazine (1.70 kg) in dimethyl formamide (DMF) (11 kg) were added triethylamine (1.52 kg) and 4-dimethyl aminopyridine (0.13 kg), and while stirring this mixture in an ice bath, methanesulfonyl chloride (1.54 kg) was added dropwise to this mixture over a period of 50 minutes, and the mixture was stirred in an ice bath for 25 minutes. After the completion of the reaction, the insoluble content was removed, and the residue was washed with DMF (1.6 kg×2). The filtrate and the washing solution were added to a mixed solution of DMF (1.63 kg), 2-mercaptobenzimidazole (1.61 kg), potassium carbonate (1.63 kg), and 18-crown-6 (0.28 kg) at 80° C., and the mixture was stirred at 80° C. for 1.5 hours. After adding water to the reaction solution, the solution was concentrated under reduced pressure, and extracted with chloroform (13 kg×3). The organic layer was washed with saturated aqueous sodium chloride, dried over anhydrous sodium sulfate, and concentrated under reduced pressure. The resulting crude product was crystallized from methanol-diisopropyl ether to give 1.92 kg of 1-[2-(benzimidazol-2-ylthio)ethyl]-4-formylpiperazine (yield 62%) as a colorless crystalline powder. Another 367 g of 1-[(2-(benzimidazol-2-ylthio)ethyl]-4-formylpiperazine (yield 11.8%) was obtained from the mother liquor of crystallization by repeating the procedure. Total yield was 2.28 kg (yield 74%).

Melting point: 146–148° C.

IR (KBr) cm$^{-1}$: 3440, 3049, 1619, 1441, 742.

$^1$H-NMR (CDCl$_3$): 2.62 (4H, dt, J=10.5, 5.3 Hz), 2.91 (2H, t, J=6.1 Hz), 3.37 (2H, t, J=6.1 Hz), 3.46 (2H, t, J=5.0 Hz), 3.65 (2H, t, J=5.0 Hz), 7.18 (1H, dd, J=7.3, 3.0 Hz), 7.21 (1H, dd, J=7.3, 3.0 Hz), 7.41–7.58 (2H, m), 8.06 (1H, s).

MS (m/z): 290 (M$^+$, 3.2), 140 (100).

Elementary analysis: as $C_{14}H_{18}N_4OS$

Calculated: C, 57.91; H, 6.25; N, 19.29; S, 11.04.

Found: C, 57.78; H, 6.30; N, 19.12; S, 11.15.

Example 2

Synthesis of 1-[2-(benzimidazol-2-ylthio)ethyl]piperazine.3 hydrochloride

1-[2-(benzimidazol-2-ylthio)ethyl]-4-formylpiperazine (1.92 kg) was suspended in methanol (4.5 kg), and 12N hydrochloric acid (2.9 kg) was added, and the mixture was stirred at 40° C. for 3 hours. To the reaction solution was added chloroform (17 kg), and the precipitated crystals were collected by filtration. The crystals were washed with chloroform to give 2.38 kg of 1-[2-(benzimidazol-2-ylthio)ethyl] piperazine.3 hydrochloride (yield 97%) as colorless crystalline powder.

Melting point: 241–246° C.

IR (KBr) cm$^{-1}$: 3374, 2938, 2647, 1630, 1522.

¹H-NMR (DMSO-d₆): 3.37–3.50 (4H, m), 3.43–3.57 (4H, m), 3.54 (2H, t, J=7.0 Hz), 3.81 (2H, t, J=7.0 Hz), 7.31 (2H, dd, J=5.9, 3.3 Hz), 7.59 (2H, dd, J=5.9, 3.3 Hz), 9.73 (2H, br s).

MS (m/z): 262 (M$^+$-3HCl, 3.1), 140 (100).

Elementary analysis: as $C_{13}H_{18}N_4S \cdot 3HCl$

Calculated: C, 42.00; H, 5.69; N, 15.07.

Found: C, 41.87; H, 5.62; N, 14.98.

Comparative Example 1

Production of 1-tert-butoxycarbonyl-4-(2-hydroxyethyl)piperazine (1a)

The synthesis was conducted according to the method described in U.S. Pat. No. 4,247,549.

Comparative Example 2

Production of 1-[2-(benzimidazol-2-ylthio)ethyl]-4-tert-butoxycarbonyl piperazine (4a)

Triethylamine (1.04 g, 10.3 mmol) and 4-dimethyl aminopyridine (104 mg, 0.854 mmol) were added to a solution of 1-tert-butoxycarbonyl-4-(2-hydroxyethyl)piperazine (2.00 g, 8.54 mmol) in tetrahydrofuran (THF) (30 mL) in an ice bath, and the solutes were dissolved by stirring. Methanesulfonyl chloride (1.37 g, 12.0 mmol) was added dropwise to the solution in the ice bath over a period of 5 minutes with stirring, and the mixture was stirred for 1 hour in an ice bath. After the completion of the reaction, the insoluble content was removed by filtration, and the thus removed insoluble content was washed with THF (10 mL×2). The filtrate and the washing solution were combined and concentrated under reduced pressure to such degree that substantially no solvent was left. The concentrate was diluted with DMF (20 mL). To the solution was added 2-mercaptobenzimidazole (1.41 g, 9.39 mmol), potassium carbonate (1.77 g, 12.8 mmol), and 18-crown-6 (226 mg, 0.854 mmol), and the mixture was stirred at 80° C. for 3 hours. The reaction solution was concentrated under reduced pressure, and the resulting concentrate was diluted and separated with ethyl acetate (10 mL) and water (50 mL). The aqueous layer was further extracted with ethyl acetate (10 mL×2), and the extract was combined with the organic layer, washed with saturated aqueous sodium chloride, and dried over anhydrous sodium sulfate. It was then purified by silica gel column chromatography (chloroform/methanol saturated with ammonia=40/1) to give 1-[2-(benzimidazol-2-ylthio)ethyl]-4-tert-butoxycarbonyl piperazine 2.02 g (64%) as colorless powdery crystals.

Melting point: 175–176° C.

IR(KBr)cm$^{-1}$: 3433, 1695, 1619, 1591, 1517.

¹H-NMR (CDCl₃): δ 1.49 (9H, s), 2.64 (4H, t, J=5.0 Hz), 2.96 (2H, t, J=5.4 Hz), 3.26 (2H, t, J=5.4 Hz), 3.61 (4H, t, J=5.0 Hz), 7.17–7.22 (2H, m), 7.40–7.65 (2H, m).

Elementary analysis: $C_{18}H_{26}N_4O_2S$

Calculated: C, 59.64; H, 7.23; N, 15.46.

Found: C, 59.63; H, 7.22; N, 15.30.

Comparative Example 3

Production of 1-[2-(benzimidazol-2-ylthio)ethyl]piperazine.3 trifluoroacetate (5a)

1-[2-(benzimidazol-2-ylthio)ethyl]-4-tert-butoxycarbonyl piperazine (13.83 g, 38.15 mmol) was dissolved in trifluoroacetic acid (75 mL) in an ice bath, and the mixture was stirred at the same temperature for 30 minutes, and after elevating the temperature to room temperature, the mixture was stirred for another 40 minutes. The reaction solution was concentrated under reduced pressure, and the resulting crystals were recrystallized from methanol-diethyether to give 15.24 g of 1-[2-(benzimidazole-2-ylthio)ethyl]piperazine.3 trifluoroacetate (66%) as pale yellow powdery crystals.

Melting point: 146–148° C.

IR(KBr)cm$^{-1}$: 3572, 3512, 1675, 1619, 1536, 1189, 1132.

¹H-NMR (DMSO-d₆): δ 3.05–3.11 (4H, m), 3.15 (2H, t, J=6.3 Hz), 3.19–3.27 (4H, m), 3.55 (2H, t, J=6.3 Hz), 7.16–7.22 (2H, m), 7.46–7.52 (2H, m), 8.75–9.10 (2H, m).

Elementary analysis: $C_{19}H_{21}F_9N_4O_6S$

Calculated: C, 37.75; H, 3.50; N, 9.27.

Found: C, 37.56; H, 3.67; N, 9.20.

As demonstrated above, the production method of the present invention using the 1-formyl-4-(2-hydroxyethyl) piperazine could improve both the yield (steps 2 and 3) and the convenience of the purification (step 2) over the conventional production method using the 1-(tert-butoxycarbonyl)-4-(2-hydroxyethyl)piperazine. In addition, in contrast to the conventional method wherein increase in the production scale had been associated with the decrease in the yield (note that the yield of compound (4a) was 64% when 2 g of compound (1a) was used while the yield dropped to 26% when 50 g of compound (1a) was used), the production method of the present invention is free from such loss in the yield with the increase in the production scale, and similar yields are obtained in both the industrial scale production and the small scale production.

What is claimed is:

1. A method for producing 1-[2-(benzimidazol-2-ylthio) ethyl]piperazine represented by the following formula (5):

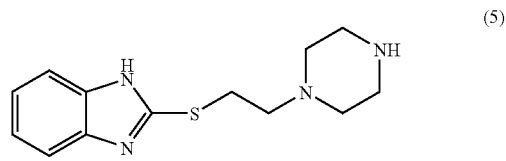

(5)

or its salt, comprising the steps of:

converting hydroxyl group in 1-formyl-4-(2-hydroxyethyl) piperazine represented by the following formula (1):

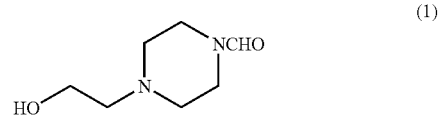

(1)

to a leaving group to produce a compound represented by the following formula (2):

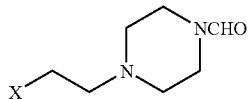
(2)

wherein X represents a leaving group;

reacting this compound with 2-mercaptobenzimidazole (3) to produce 1-[2-(benzimidazol-2-ylthio)ethyl]-4-formylpiperazine represented by the following formula (4):

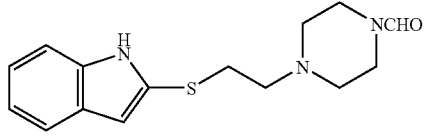
(4)

and removing the formyl group therefrom.

2. The method according to claim 1 wherein the 1-formyl-4-(2-hydroxyethyl) piperazine represented by the following formula (1):

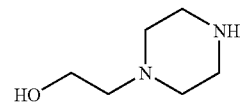
(1)

is produced by converting amino group of 1-(2-hydroxyethyl) piperazine represented by the following formula (6)

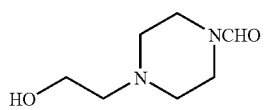
(6)

to formyl group.

* * * * *